United States Patent
Sugiura

(10) Patent No.: US 10,520,464 B2
(45) Date of Patent: Dec. 31, 2019

(54) GAS SENSOR AND METHOD FOR MANUFACTURING THE SAME

(71) Applicant: DENSO CORPORATION, Kariya, Aichi-pref. (JP)

(72) Inventor: Kei Sugiura, Kariya (JP)

(73) Assignee: DENSO CORPORATION, Kariya (JP)

( * ) Notice: Subject to any disclaimer, the term of this patent is extended or adjusted under 35 U.S.C. 154(b) by 209 days.

(21) Appl. No.: 15/535,865

(22) PCT Filed: Dec. 17, 2015

(86) PCT No.: PCT/JP2015/085321
§ 371 (c)(1),
(2) Date: Jun. 14, 2017

(87) PCT Pub. No.: WO2016/098844
PCT Pub. Date: Jun. 23, 2016

(65) Prior Publication Data
US 2017/0363570 A1 Dec. 21, 2017

(30) Foreign Application Priority Data
Dec. 17, 2014 (JP) .................. 2014-254877

(51) Int. Cl.
*G01N 27/407* (2006.01)
*G01N 27/41* (2006.01)
*G01N 27/419* (2006.01)

(52) U.S. Cl.
CPC ..... *G01N 27/4075* (2013.01); *G01N 27/4073* (2013.01); *G01N 27/41* (2013.01); *G01N 27/419* (2013.01)

(58) Field of Classification Search
CPC ....... G01N 27/404–407; G01N 27/409; G01N 27/419; G01N 27/41; G01N 27/4073; G01N 27/4075; G01N 27/4045; G01N 27/4074; F01N 2560/00–20; F01N 2550/00–24;
(Continued)

(56) References Cited

U.S. PATENT DOCUMENTS

| | | | |
|---|---|---|---|
| 4,515,674 A | * | 5/1985 | Takahashi .............. C25D 13/22 204/290.01 |
| 5,421,984 A | | 6/1995 | Saito et al. |

(Continued)

FOREIGN PATENT DOCUMENTS

| | | |
|---|---|---|
| JP | 11-237366 | 8/1999 |
| JP | 2003-130842 | 5/2003 |

*Primary Examiner* — Gurpreet Kaur
(74) *Attorney, Agent, or Firm* — Nixon & Vanderhye PC

(57) ABSTRACT

A gas sensor having a reliable measurement accuracy for specific gases even if a pump electrode is heated and a method for manufacturing the same are provided. The gas sensor is provided with a measurement target gas chamber, a reference gas chamber, a solid electrolyte, a pump electrode, a sensor electrode, a reference electrode and a heater. The pump electrode includes Pt, Au and an aggregate. After the gas sensor has been manufactured, in a state that the pump electrode has not been heated to an activation temperature of the solid electrolyte yet, in the pump electrode, a pore is 5.2 vol % or less, a surface roughness Ra is 0.5 µm to 9.1 µm, and a content ratio of the aggregate is 4.9 vol % or more.

7 Claims, 11 Drawing Sheets

(58) Field of Classification Search
CPC ... G01M 15/10; G01M 15/102; G01M 15/104
See application file for complete search history.

(56) References Cited

U.S. PATENT DOCUMENTS

| | | | |
|---|---|---|---|
| 2002/0070110 A1* | 6/2002 | Naito | G01N 27/407 |
| | | | 204/426 |
| 2005/0181267 A1* | 8/2005 | Mitsuta | H01M 8/0284 |
| | | | 429/483 |
| 2006/0231397 A1* | 10/2006 | Nakagaki | G01N 27/4045 |
| | | | 204/431 |
| 2009/0242401 A1 | 10/2009 | Horisaka et al. | |
| 2015/0129435 A1* | 5/2015 | Franaszczuk | G01N 27/49 |
| | | | 205/785.5 |
| 2016/0061768 A1* | 3/2016 | Nakasone | G01N 27/301 |
| | | | 204/412 |
| 2018/0003670 A1* | 1/2018 | Oya | G01N 27/41 |

\* cited by examiner

GAS SENSOR AND METHOD FOR MANUFACTURING THE SAME

This application is the U.S. national phase of International Application No. PCT/JP2015/085321 filed Dec. 17, 2015 which designated the U.S. and claims priority to Japanese Patent Application No. 2014-254877 filed on Dec. 17, 2014, the entire contents of each of which are hereby incorporated herein by reference.

TECHNICAL FIELD OF THE DISCLOSURE

This disclosure relates to a gas sensor for determining the concentration of specific gases included in measurement target gases and a method for manufacturing the gas sensor.

BACKGROUND OF THE DISCLOSURE

There is known a gas sensor for determining the concentration of NOx or the like included in exhaust gas or the like of automobiles (refer to patent document 1). The gas sensor is provided with a measurement target gas chamber, a reference gas chamber and a solid electrolyte. The measurement target gas chamber introduces measurement target gases such as the exhaust gases. The reference gas chamber introduces reference gases such as atmospheric air. The solid electrolyte is disposed between the measurement target gas chamber and the reference gas chamber.

The solid electrolyte is composed of a material such as zirconia showing oxygen ion conductivity. A pump electrode and a sensor electrode are formed on the surface of the solid electrolyte at a side of the measurement target gas chamber. In addition, a reference electrode is formed on the surface of the solid electrolyte at a side of the reference gas chamber.

A pump cell for reducing oxygen included in measurement target gases is formed with the pump electrode, the solid electrolyte and the reference electrode. In addition, a sensor cell for determining the concentration of specific gases such as NOx included in the measurement target gases is formed with the sensor electrode, the solid electrolyte and the reference electrode. The sensor cell has sensitivity to oxygen and the specific gases. Therefore, the gas sensor is constructed so that the concentration of the specific gases is determined using the sensor cell after reducing an oxygen concentration included in the measurement target gases using the pump cell.

The pump electrode is composed of Pt—Au alloy or the like having a property of reducing oxygen molecules to oxygen ions. Oxygen molecules included in the measurement target gases are reduced to oxygen ions on the surface of the pump electrode. After that, oxygen ions are discharged from the reference chamber via the inside of the solid electrolyte.

Pores, through which the measurement target gas may pass, are formed inside the pump electrode. Thereby, a contact area between the pump electrode and the measurement target gases is increased, and an ability of discharging oxygen included in the measurement target gases is raised.

RELATED ART

Patent Document

[Patent Document 1] Japanese Unexamined Patent Application Publication No. 2009-244117.

SUMMARY OF THE DISCLOSURE

However, the present inventor noticed that an oxygen discharge capacity of the pump cell may be gradually reduced during use of the gas sensor after manufacturing and/or performing of a high temperature durability test. That is, when the gas sensor is used and the high temperature durability test is performed, the solid electrolyte needs to be heated to an activation temperature using a heater or the like. The pump electrode is heated by the heater. A melting point of alloy particles constituting the pump electrode is relatively low because the pump electrode includes low-melting-point Au. Therefore, when heated for a long time, the alloy particles are agglomerated. The pores may be filled with the agglomerated alloy particles. Accordingly, the contact area between the pump electrode and the measurement target gases may be decreased, and the ability of discharging oxygen included in the measurement target gases may be gradually reduced. Thereby, the measurement target gases having the high oxygen concentration are gradually transferred to the sensor cell. Therefore, a measurement accuracy of the specific gases may be gradually reduced due to the sensor cell.

The present disclosure provides a gas sensor of which the measurement accuracy to the specific gases becomes difficult to be reduced even when the pump electrode is heated, and provides a method of manufacturing the gas sensor.

Means for Solving the Problems

A first aspect of the present disclosure is a gas sensor determining a concentration of specific gases included in measurement target gases. The gas sensor has a measurement target gas chamber, a reference gas chamber, a solid electrolyte, a pump electrode, a sensor electrode and a reference electrode. The measurement target gases are supplied into the measurement target gas chamber. Reference gases are supplied into the reference chamber. The solid electrolyte has oxygen ion conductivity, and is disposed between the measurement target gas chamber and the reference gas chamber. The pump electrode and the sensor electrode are formed on the surface on the solid electrolyte at a side of the measurement target gas chamber. The reference electrode is formed on the surface of the solid electrolyte at a side of the reference gas chamber. A pump cell is composed of the solid electrolyte, the pump electrode and the reference electrode. The pump cell may reduce an oxygen concentration included in the measurement target gases. A sensor cell is composed of the solid electrolyte, the sensor electrode and the reference electrode. The sensor cell determines a concentration of the specific gases included in the measurement target gases after the pump cell reduces the oxygen concentration. The pump electrode includes Pt, Au and an aggregate. After the gas sensor has been manufactured, when the pump electrode has not been heated to an activation temperature of the solid electrolyte yet, in the pump electrode, a pore is 5.2 vol % or less, and a surface roughness Ra is set in a range of 0.5 μm to 9.1 μm, and a content ratio of the aggregate is 4.9 vol % or more.

A second embodiment of the present disclosure is a method for manufacturing the gas sensor having a printing process, a surface working process, an assembling process and a calcination process. In the printing process, a pump electrode green body, which is the unbaked pump electrode, is printed on a surface of a solid electrolyte which is an unbaked solid electrolyte. In the surface working process, the surface of the pump electrode green body is roughened by pressing an irregularity-forming tool to the pump electrode green body. Fine irregularities are formed on the surface of the irregularity-forming tool. In the assembling process, a sensor green body, which is an unbaked gas sensor, is assembled using the pump electrode green body. In the calcination process, the gas sensor is formed by calcinating the sensor green body.

DETAILED DESCRIPTION OF THE DISCLOSURE

Figure 1:
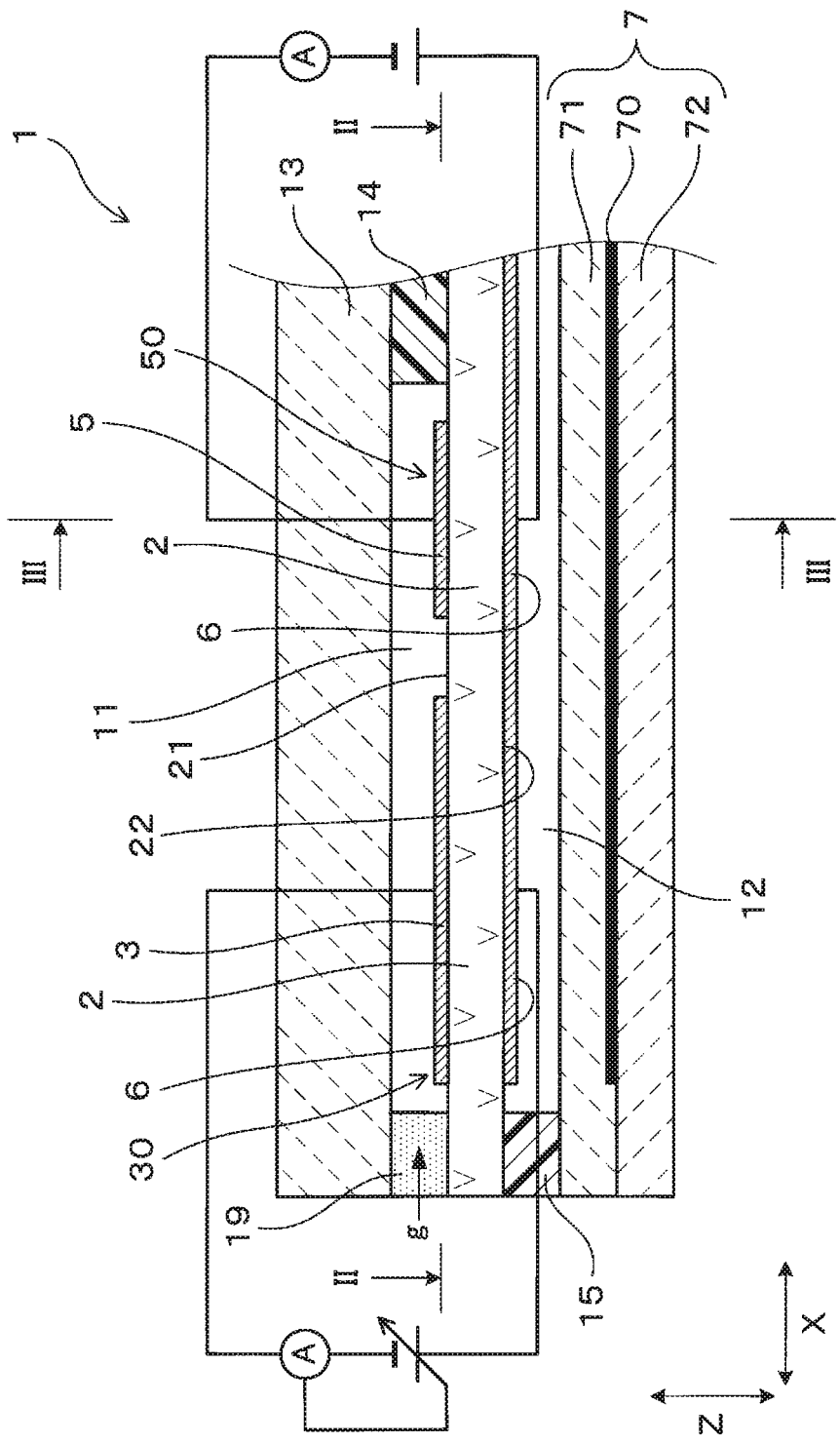
FIG. 1 shows a cross-sectional view of a gas sensor according to a first embodiment.

A gas sensor may be a NOx sensor for determining a concentration of NOx included in exhaust gases discharged from automobiles.

EMBODIMENTS

First Embodiment

An embodiment according to the gas sensor will be described using FIGS. 1 to 8. The present gas sensor 1 is used for determining a concentration of specific gases included in measurement target gases g. As shown in FIGS. 1 to 4, the gas sensor 1 is provided with a measurement target gas chamber 11, a reference gas chamber 12, a solid electrolyte 2, a pump electrode 3, a sensor electrode 5 and a reference electrode 6. The measurement target gases g are supplied to the measurement target gas chamber 11. Reference gases such as atmospheric air are supplied to the reference chamber 12.

The solid electrolyte 2 has oxygen ion conductivity. The solid electrolyte 2 is disposed between the measurement target gas chamber 11 and the reference chamber 12.

The pump electrode 3 and the sensor electrode 5 are formed on a surface 21 of the solid electrolyte 2 at a side of the measurement target gas chamber 11.

The reference electrode 6 is disposed on a surface 22 of the solid electrolyte 2 at a side of the reference chamber 12.

A pump cell 30 is composed of the solid electrolyte 2, the pump electrode 3 and the reference electrode 6. The pump cell 30 reduces an oxygen concentration included in the measurement target gases. In addition, a sensor cell 50 is composed of the solid electrolyte 2, the sensor electrode 5 and the reference electrode 6. The sensor cell determines a concentration of the specific gases included in the measurement target gases g after the pump cell 30 reduces the oxygen concentration.

Figure 5:
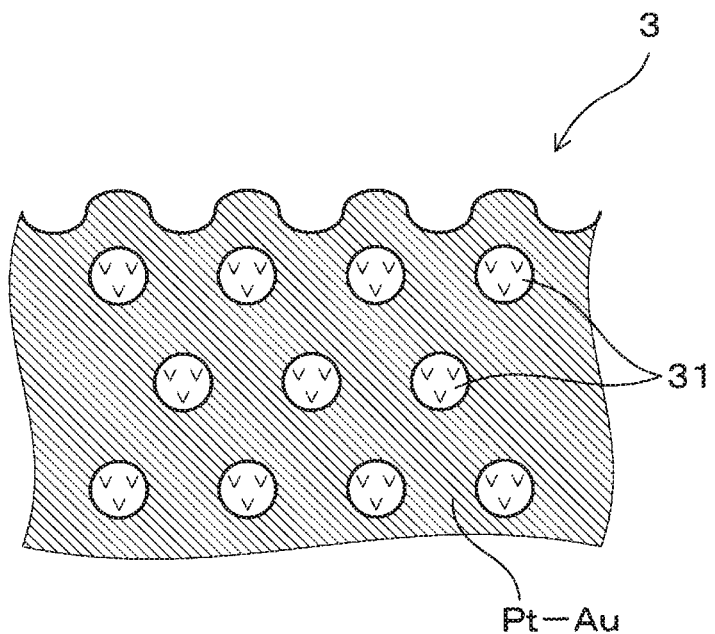
FIG. 5 shows a conceptual diagram of a cross section of a pump electrode according to the first embodiment.

As shown in FIG. 5, the pump electrode 3 includes Pt, Au and an aggregate 31. After the gas sensor 1 has been manufactured, in a state that the pump electrode 3 has not been heated to an activation temperature of the solid electrolyte 2 yet (hereinafter referred to as an initial state), in the pump electrode 3, a pore is set to be 5.2 vol % or less, and a surface roughness Ra is set in a range of 0.5 μm to 9.1 μm, and a content ratio of the aggregate 31 is set to be 4.9 vol % or more.

The gas sensor 1 of the present embodiment is the NOx sensor for determining the concentration of NOx included in the exhaust gases discharged from engines of the automobiles.

Figure 2:
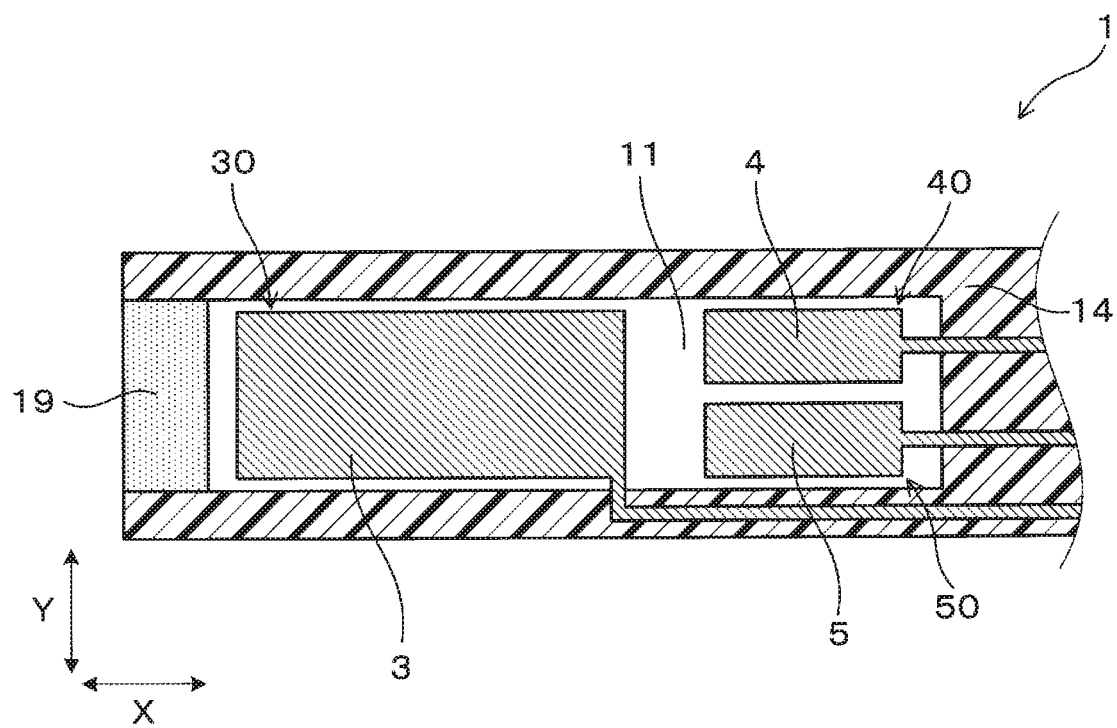
FIG. 2 shows a cross-sectional view taken across a line II-II in FIG. 1.
Figure 3:
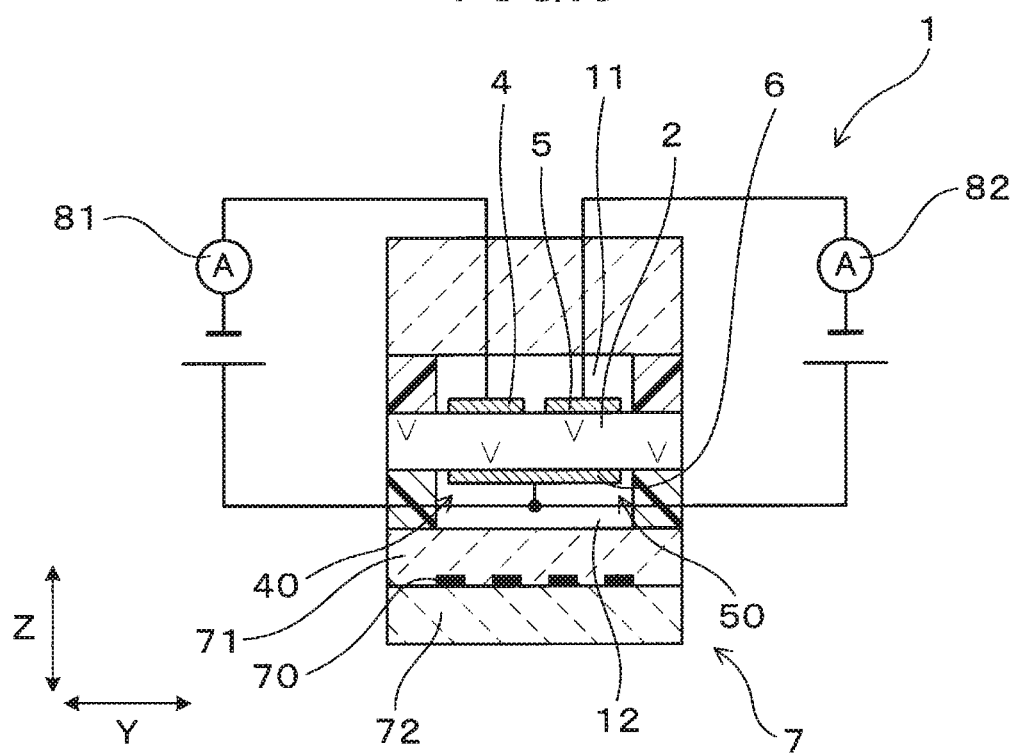
FIG. 3 shows a cross-sectional view taken across a line III-III in FIG. 1.
Figure 4:
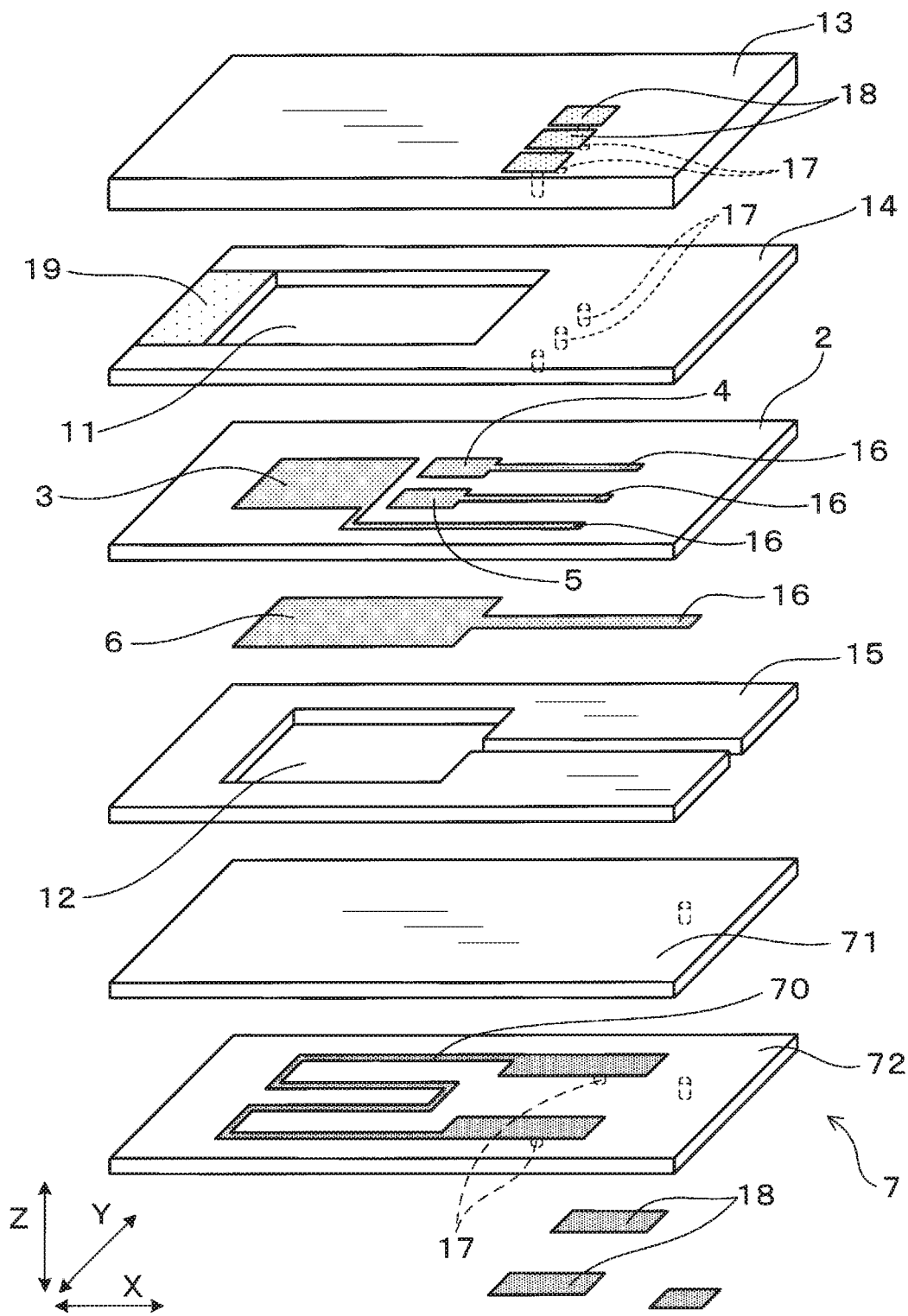
FIG. 4 shows an exploded perspective view of the gas sensor according to the first embodiment.

As shown in FIGS. 2 to 4, a monitor electrode 4 is formed on the surface 21 of the solid electrolyte 2 at the side of the measurement target gas chamber 11 other than the pump electrode 3 and the sensor electrode 5. The monitor cell 40 is formed by the monitor electrode 4, the solid electrolyte 2 and the reference electrode 6. The monitor cell 40 is a cell for determining a concentration of residual oxygen included in measurement target gases g after reducing the oxygen concentration using the pump cell 30.

As described above, the pump electrode 3 includes Pt, Au and the aggregate 31. A content ratio of pt is, for example, set in a range of 48.5 wt % to 98.5 wt %, and a content ratio of au is, for example, set in a range of 0.2 wt % to 9.9 wt %. The aggregate 31 is composed of a powder such as zirconia. The particle diameter of the aggregate 31 is, for example, set in a range of 0.5 μm to 5.0 μm. In the present embodiment, the content ratio of the aggregate 31 is set in a range of 4.9 vol % to 75.0 vol %.

The monitor electrode 4 has the same composition as the pump electrode 3. In addition, the sensor electrode 5 is composed of a Pt—Rh cermet electrode. The Pt—Rh cermet electrode has properties of degrading oxygen and NOx.

When discharging oxygen using the pump cell 30, a direct-current voltage (hereinafter referred to as a pump voltage) is applied between the pump electrode 3 and the reference electrode 6 so that the reference electrode 6 has a high potential. When applied the pump voltage between the pump electrode 3 and the reference electrode 6, oxygen included in the measurement target gases g is reduced to oxygen ions at the pump electrode 3, and is discharged to the reference chamber 12 via the solid electrolyte 2.

In the present embodiment, when oxygen included in the measurement target gases g is discharged using the pump cell 30, a concentration A of residual oxygen included in the measurement target gases g is determined using the monitor cell 40. In addition, a concentration B of a total of residual oxygen included in the measurement target gases g and the specific gases is determined using the sensor cell 50. Then, the concentration of the specific gases subtracting the concentration A from the concentration B is determined.

As shown in FIG. 3, the monitor cell 40 and the sensor cell 50 are respectively connected with a current sensor 81 and a current sensor 82. A current passing through the monitor cell 40 (hereinafter referred to as a monitor current) is determined using the current sensor 81. A current passing through the sensor cell 50 (hereinafter referred to as a sensor current) is determined using the current sensor 82.

Residual oxygen included in the measurement target gases g is reduced to oxygen ions at the monitor electrode 4, and is then discharged to the reference gas chamber 12 via the solid electrolyte 2. At this moment, the monitor current passes through the monitor cell 40. The concentration A of residual oxygen is determined by determining the monitor current. In addition, the sensor electrode 5 allows residual oxygen and residual NOx included in the measurement target gases g to be reduced to oxygen ions. Then, oxygen ions are discharged to the reference gas chamber 12 via the solid electrolyte 2. At this moment, the sensor current passes through the sensor cell 50. The total concentration B of residual oxygen and NOx (specific gases) included in the measurement target gases g by determining of the sensor current.

Incidentally, the monitor cell 40 and the sensor cell 50 are slightly different from each other in a sensitivity relative to oxygen. Therefore, when there is a large amount of residual oxygen included in the measurement target gases g, the concentration of the specific gases may not be accurately determined. Accordingly, if the oxygen concentration included in the measurement target gases g is reduced using the pump cell 30 as much as possible, the concentration of the specific gases may be accurately determined.

In addition, the gas sensor 1 is, as shown in FIG. 4, provided with a plurality of ceramic boards 13 to 15 and a heater 7. The solid electrolyte 2, the pump electrode 3, the monitor electrode 4, sensor electrode 5 and the reference electrode 6 are heated using the heater 7.

A plurality of external connection terminals 18 are formed on surfaces of the ceramic board 13 and the heater 7. In addition, the pump electrode 3 and the monitor electrode 4 and the like are respectively connected with each of wirings 16. Each of the external connection terminals 18 is connected with the wiring 16 via through plugs 17 penetrating the ceramic boards 13 and 14.

In addition, the gas sensor 1 is provided with a diffusion resistance part 19 composed of alumina or the like. An inflow velocity of the measurement target gases g entering from outside of a sensor to the measurement target gas chamber 11 is restricted using the diffusion resistance part 19.

The heater 7 is provided with two heater boards 71 and 72 made of ceramics and a heat generator 70 disposed between the two heater boards 71 and 72. The through plugs 17 for electrically connecting the external connection terminal 18 with the heat generator 70 are formed on the heater boards 71 and 72.

Next, a manufacturing method of the gas sensor 1 will be described. In the present embodiment, the gas sensor 1 is manufactured by performing a printing process (refer to FIG. 6), a surface working process (refer to FIG. 7), an assembling process (refer to FIG. 8) and a calcination process.

Figure 6:
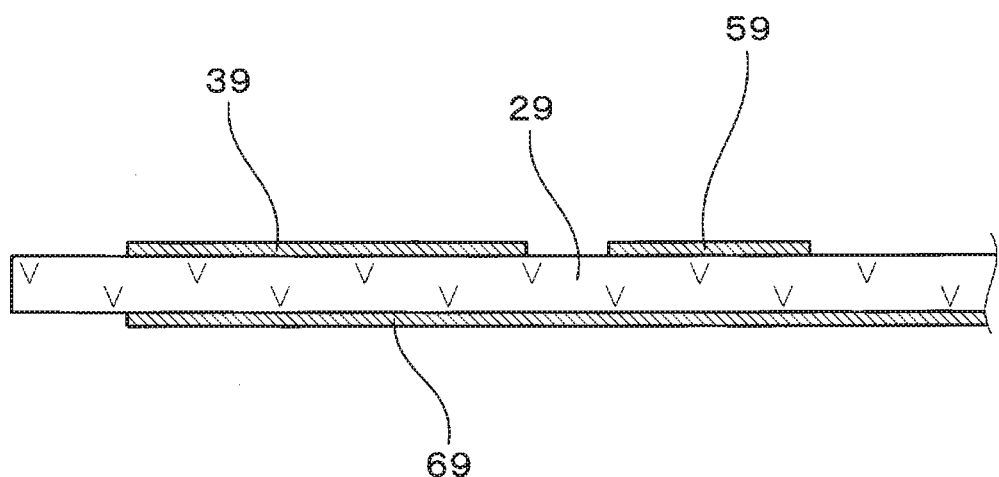
FIG. 6 shows an explanatory drawing of a method for manufacturing the gas sensor according to the first embodiment.

In the printing process, as shown in FIG. 6, a pump electrode green body 39, which is the unbaked pump electrode 3, is printed on a surface of a solid electrolyte green body 29, which is the unbaked solid electrolyte 2. The pump electrode green body 39 includes Pt, Au, zirconia particles as the aggregate 31, resins and solvents. In the printing process, a sensor electrode green body 59, a monitor electrode green body (not shown) and a reference electrode green body 69 are also printed on the solid electrolyte green body 29. The sensor electrode green body 59 is the unbaked sensor electrode 5. The monitor electrode green body is the unbaked monitor electrode 4. The reference electrode green body 69 is the unbaked reference electrode 6.

Figure 7:
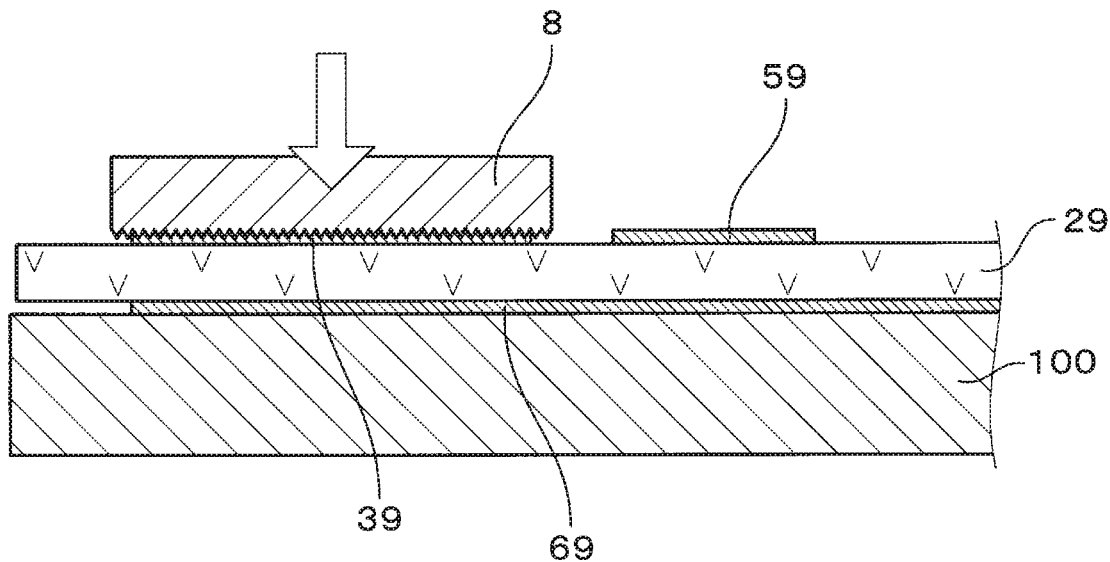
FIG. 7 shows an explanatory drawing of a surface working process in the method for manufacturing the gas sensor according to the first embodiment.

Next, the surface working process will be performed. In this process, as shown in FIG. 7, the solid electrolyte green body 29 is mounted on a loading stand 100. In addition, an irregularity-forming tool 8 is pressed to the pump electrode green body 39. Fine irregularity is formed on the surface of the irregularity-forming tool 8. Thereby, the surface of the pump electrode green body 39 is roughened. In this case, after performing the calcination process described hereafter, the surface roughness of the pump electrode green body is adjusted so that the surface roughness Ra of the pump electrode 3 is set in the range of 0.5 μm to 9.1 μm.

Figure 8:
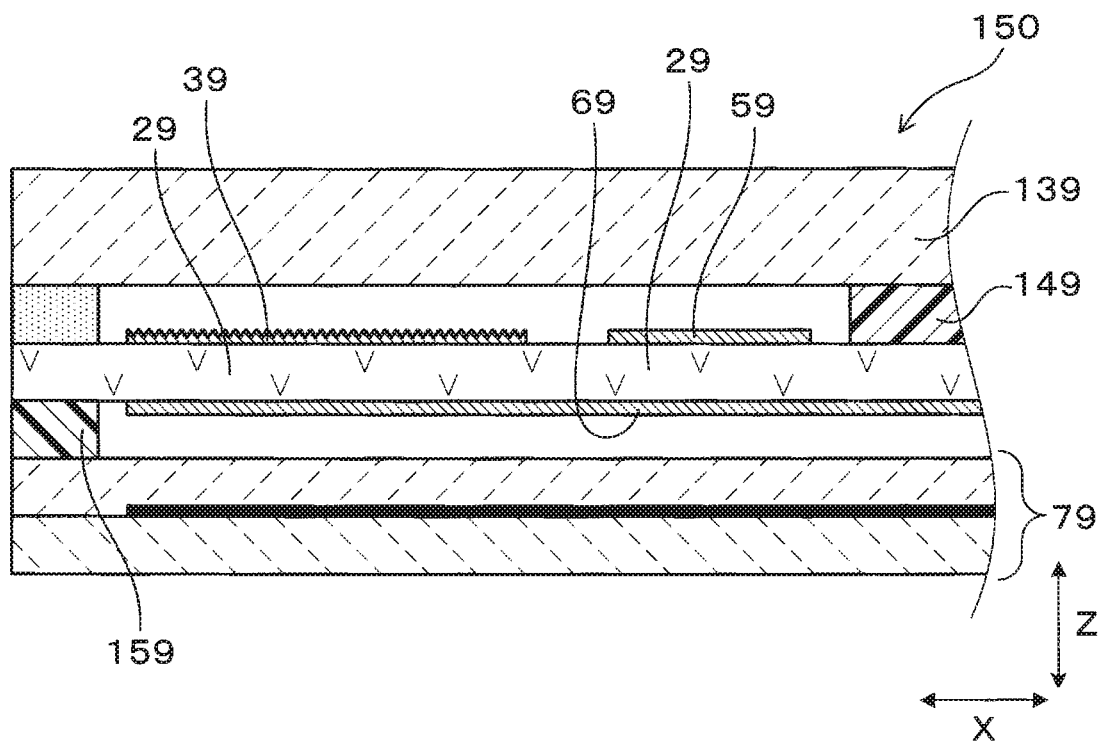
FIG. 8 shows an explanatory drawing of an assembling process in the method for manufacturing the gas sensor according to the first embodiment.

Next, the assembling process will be performed. In this process, as shown in FIG. 8, a sensor green body 150, which is the unbaked gas sensor 1, is assembled using the solid electrolyte green body 29. That is, the sensor green body 150 is formed by assembling unbaked ceramic boards 139, 149 and 159, an unbaked heater 79 and the solid electrolyte green body 29.

After this, the calcination process will be performed. In this process, the sensor green body 150 is supplied into a baking furnace, and is calcinated. Thereby, the gas sensor 1 is manufactured. The calcination process is performed in a low-oxygen atmospheric air of which the oxygen concentration (i.e. $O_2$ gas concentration) is 2 volume % or less. In addition, a calcination temperature is set in a range of 1400° C. to 1500° C.

As described above, the pump electrode green body 39 is subjected to a process for roughening a surface (a surface working process). However, the surface of the pump electrode green body 39 becomes slightly smooth due to the heat of the calcination process. As a result, the surface roughness Ra of the baked pump electrode 3 becomes in the range of 0.5 μm to 9.1 μm.

Functions and effects of the present embodiment will be described. After the gas sensor 1 of the present embodiment has been manufactured, a porosity of the pump electrode 3 is set to be 5.2 vol % or less in the state that the pump electrode 3 has not been heated to the activation temperature of the solid electrolyte 2 yet.

Therefore, even if the pump electrode 3 is heated, measurement accuracy of a specific gases concentration is unlikely to be reduced. That is, in the present embodiment, the pore of the pump electrode 3 is set to be low before being heated. Therefore, after the gas sensor 1 has been manufactured, even if the pump electrode 3 is heated, a problem in which pores of the pump electrode 3 become clocked is unlikely to occur. Because the number of the pores is originally small, alloy particles constituting the pump electrode 3 are agglomerated due to the heat. Accordingly, a contact area between the pump electrode 3 and the measurement target gases g is reduced due to being heated, and a problem in which oxygen discharge ability is gradually reduced is unlikely to occur. Therefore, the measurement accuracy of the specific gases concentration is unlikely to be reduced due to the sensor cell 50.

In addition, after the gas sensor 1 of the present embodiment has been manufactured, the surface roughness Ra of the pump electrode 3 is set in the range of 0.5 µm to 9.1 µm in the state that the pump electrode 3 has not been heated to the activation temperature of the solid electrolyte 2 yet.

When the pore of the pump electrode 3 is reduced to the above-described 5.2 vol % or less, the measurement target gases g is hardly supplied into the pores because the number of the pores is small. Therefore, it is difficult for the measurement target gases g to contact the surface of the pores. However, when the surface roughness Ra of the pump electrode 3 is set in the range of 0.5 µm to 9.1 µm, the surface area of the pump electrode 3 may become sufficiently large. The measurement target gases g may be sufficiently contacted with the surface of the pump electrode 3. Therefore, the ability of discharging oxygen included in the measurement target gases g may be raised.

A critical significance of the surface roughness Ra will be described. When the surface roughness Ra is over 9.1 µm, the surface of the pump electrode 3 may become gradually smooth while heated. In addition, the ability of discharging oxygen may be gradually reduced. Therefore, the surface roughness Ra of the pump electrode 3 needs to be 9.1 µm or less.

When the surface roughness Ra of the pump electrode 3 is less than 0.5 µm, the surface area of the pump electrode 3 is difficult to be secured sufficiently. In addition, the ability of discharging oxygen becomes difficult to raise. In addition, when the surface roughness Ra is less than 0.5 µm, Au atoms migrate to the surface of the pump electrode 3 due to heat during use of the gas sensor 1. Then, the Au concentration of the surface of the pump electrode 3 may be gradually increased. That is, Au easily moves to the surface.

Therefore, when the surface area of the pump electrode 3 is small, for example, the surface roughness Ra is less than 0.5 µm, Au may not excessively move to the surface of the pump electrode 3 due to the heat in the calcination process. After the gas sensor 1 has been manufactured, Au moves to the surface of the pump electrode 3 due to heat generated from the heater 7 while the gas sensor 1 is used and a high temperature durability test is performed. The pump voltage of the pump cell 30 is set so that the ability of discharging oxygen is the highest. When the Au concentration of the surface of the pump electrode 3 is gradually increased during use of the gas sensor 1, a value of the pump voltage that may have the highest ability of discharging oxygen may be changed. Therefore, oxygen may not be sufficiently discharged at an original set pump voltage. However, when the surface roughness Ra of the pump electrode 3 is 0.5 µm or more, the above-described problem is unlikely to occur.

In addition, in the present embodiment, the content ratio of the aggregate 31 included in the pump electrode 3 is set to be 4.9 vol % or more. When the content ratio of the aggregate 31 is set to be less than 4.9 vol %, the surface of the pump electrode 3 may become gradually smooth while heated. Therefore, the contact area between the pump electrode 3 and the measurement target gases g may be decreased, and the ability of discharging oxygen may be gradually reduced. However, when the content ratio of the aggregate 31 is set to be 4.9 vol % or more, the surface of the pump electrode 3 is unlikely to be deformed when being heated. In addition, a problem of reducing the ability of discharging oxygen gradually may be reduced.

In addition, in the present embodiment, the content ratio of the aggregate 31 included in the pump electrode 3 is set to be 75.0 vol % or less. When the content ratio of the aggregate 31 is set to be 75.0 vol % or less, the increase of the electric resistance of the pump electrode 3 excessively may be reduced.

In addition, in the method for manufacturing the gas sensor 1, the above-described surface working process (refer to FIG. 7) will be performed. Therefore, the surface roughness Ra of the pump electrode 3 after performing the calcination process may be easily set in the range of 0.5 µm to 9.1 µm.

In addition, the calcination process of the present embodiment is performed in a low-oxygen atmospheric air of which the oxygen concentration is 2 volume % or less. In addition, the calcination temperature is set in the range of 1400° C. to 1500° C.

Therefore, a pore of the pump electrode 3 after calcinating can be easily set to be 5.2 vol % or less, and the surface roughness Ra of the pump electrode 3 can be easily set in the range of 0.5 µm to 9.1 µm. When the calcination temperature is less than 1400° C., the pores easily remain in the pump electrode 3. Because the calcination temperature is not sufficiently high, mutual diffusion between the alloy particles in the pump electrode 3 is difficult to be progressed. Therefore, the pore after calcinating easily becomes over 5.2 vol %.

In addition, when the calcination temperature is over 1500° C., the surface of the pump electrode 3 may become Smooth due to heat because the calcination temperature is too high, a surface roughness Ra of the pump electrode 3 after calcinating easily becomes less than 0.5 µm.

In addition, when an oxygen concentration in the baking furnace exceeds 2%, the pores easily remain in the pump electrode 3 because mutual diffusion between the alloy particles in the pump electrode 3 is unlikely to be progressed. Therefore, the pore after calcinating easily becomes over 5.2 vol %. In addition, when the oxygen concentration in the baking furnace is over 2%, Au is easily sublimed from the surface of the pump electrode 3 while heated. Therefore, the Au concentration of the surface of the pump electrode 3 after calcinating is decreased, and the ability to discharge oxygen included in the measurement target gases g is easily reduced.

As mentioned above, according to the present embodiment, even if the pump electrode is heated, a gas sensor of which the measurement accuracy of the specific gases is unlikely to be reduced, and a method for manufacturing the gas sensor, can be provided.

Incidentally, as shown in FIG. 1, in the present embodiment, the pump cell 30 and the sensor cell 50 are formed on a single solid electrolyte 2. The present disclosure is not limited to the present embodiment. That is, preparing two solid electrolytes 2, and the pump cell 30 and the sensor cell 50 may also be formed on the two respective solid electrolytes 2. In addition, in the present embodiment, as shown in FIG. 1, the pump cell 30 and the sensor cell 50 have the same reference electrode as each other. However, the pump cell 30 may also be formed independently.

Experimental Example 1

An experiment was performed for confirming an effect of the present disclosure. First, a plurality of the gas sensors 1 having configurations described in the first embodiment were manufactured. A surface roughness of each of the gas sensors 1 and a pore of each of the gas sensors 1 were respectively adjusted to values shown in the following Table 1. Samples 1 to 4 belong to the present disclosure. Comparative samples 1 to 5 do not belong to the present disclosure. In the comparative samples 1 to 5, because each of the pore in an initial state is over 5.2 vol %, the comparative samples 1 to 5 are not belong to the present disclosure.

TABLE 1

| | Surface roughness μm | Aggregate vol % | Porosity vol % | Current change rate ΔI | | Durability | |
| --- | --- | --- | --- | --- | --- | --- | --- |
| | | | | $\Delta I_A$ % | $\Delta I_B$ % | variation δI % | Resistance mΩ |
| Sample 1 | 0.5 | 30 | 5 | 1.7 | 1.8 | 0.1 | No data |
| Sample 2 | 5 | 30 | 3 | 1.5 | 1.6 | 0.1 | No data |
| Sample 3 | 5 | 30 | 5 | 1.5 | 1.6 | 0.1 | 23 |
| Sample 4 | 9 | 30 | 5.1 | 1.5 | 1.6 | 0.1 | No data |
| Comparative sample 1 | 5 | 30 | 10 | 1.4 | 2.9 | 1.5 | 20 |
| Comparative sample 2 | 0.5 | 30 | 15 | 1.6 | 4 | 2.4 | No data |
| Comparative sample 3 | 0.5 | 30 | 25 | 1.5 | 4.1 | 2.6 | No data |
| Comparative sample 4 | 9 | 30 | 13 | 1.5 | 3.8 | 2.3 | No data |
| Comparative sample 5 | 9 | 30 | 22 | 1.4 | 4.2 | 2.8 | No data |

In addition, a current is applied to a heater 7 of each of samples and the solid electrolyte 2 is heated to 900° C. This condition is kept for 20 hours. Then, it is investigated to what extent a measurement accuracy of specific gases is reduced before and after heating. An investigation method will be described below.

Figure 9:
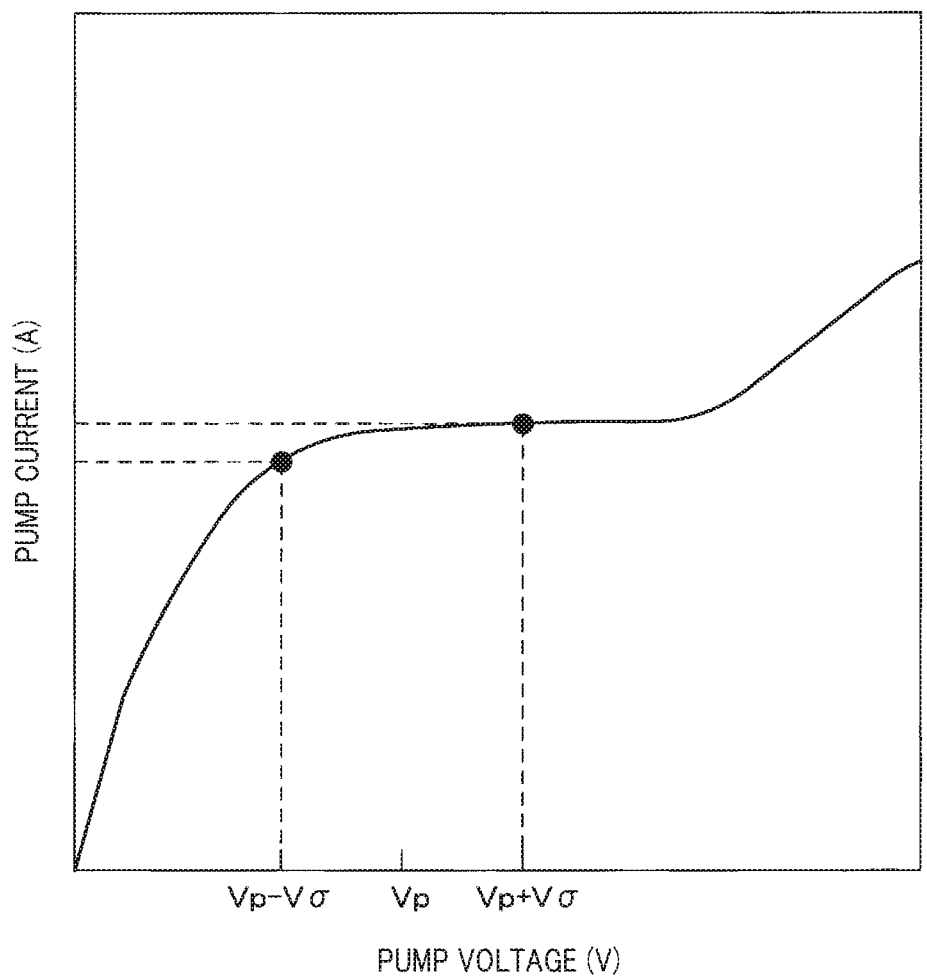
FIG. 9 a pattern graph showing relations between a pump voltage and a pump current before heating at 900° C. for 20 hours according to an experimental example 1.

First, before heating for 20 hours, a result of investigating a relationship between a pump voltage and a pump current using measurement target gases g including oxygen and NOx is shown in FIG. 9. As shown in FIG. 9, a pump cell 30 has a range where the pump current is approximately constant regardless of the pump voltage. The range is a range where oxygen may be sufficiently discharged using the pump cell 30. When the pump voltage is less than Vp−Vσ, oxygen is difficult to discharge. Therefore, the pump current is reduced. In addition, when the pump voltage is over Vp+Vσ, the specific gases (NOx) included in the measurement target gases g are decomposed. Thereby, the pump current flows. Thus, the pump cell 30 has a pump voltage range (Vp±Vσ) optimum for efficiently discharging oxygen without decomposing the specific gases. In this pump voltage range, the gas sensor 1 is used.

Figure 10:
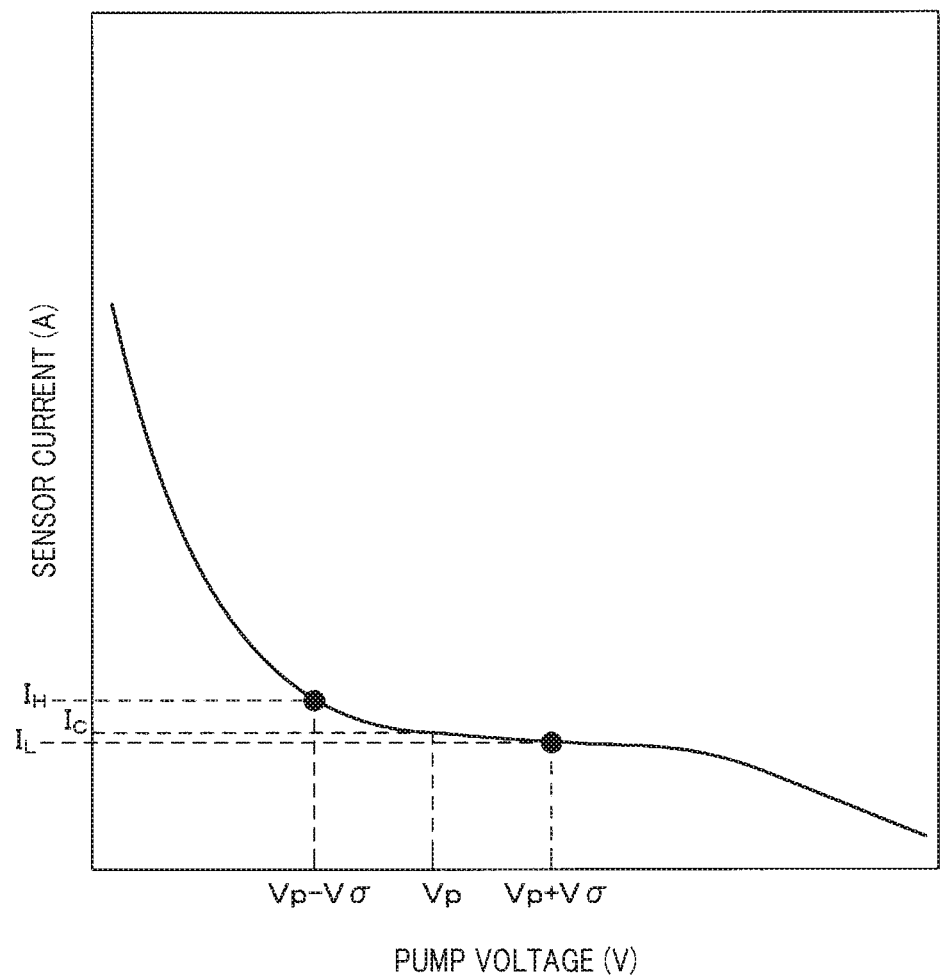
FIG. 10 a pattern graph showing relations between the pump voltage and a sensor current before heating at 900° C. for 20 hours according to the experimental example 1.

Next, before heating for 20 hours, a result of investigating a relationship between the pump voltage and the pump current is shown in FIG. 10. As shown in FIG. 10, when the pump voltage range is Vp±Vσ, the sensor current is approximately constant. That is because when the pump voltage is Vp±Vσ, oxygen included in the measurement target gases g may be sufficiently discharged using the pump cell 30. Therefore, measurement target gases g having a sufficiently low oxygen concentration may be transmitted to the sensor cell 50. Accordingly, in this pump voltage range, the concentration of the specific gases may be determined with high accuracy.

When the pump voltage is less than Vp−Vσ, a discharge efficiency of oxygen using the pump cell 30 is reduced. Therefore, measurement target gases g having the high oxygen concentration are transmitted to the sensor cell 50, and a high sensor current flows. In addition, when the pump voltage is over Vp+Vσ, the specific gases (NOx) is decomposed using the pump cell. Therefore, the sensor current is reduced.

Figure 11:
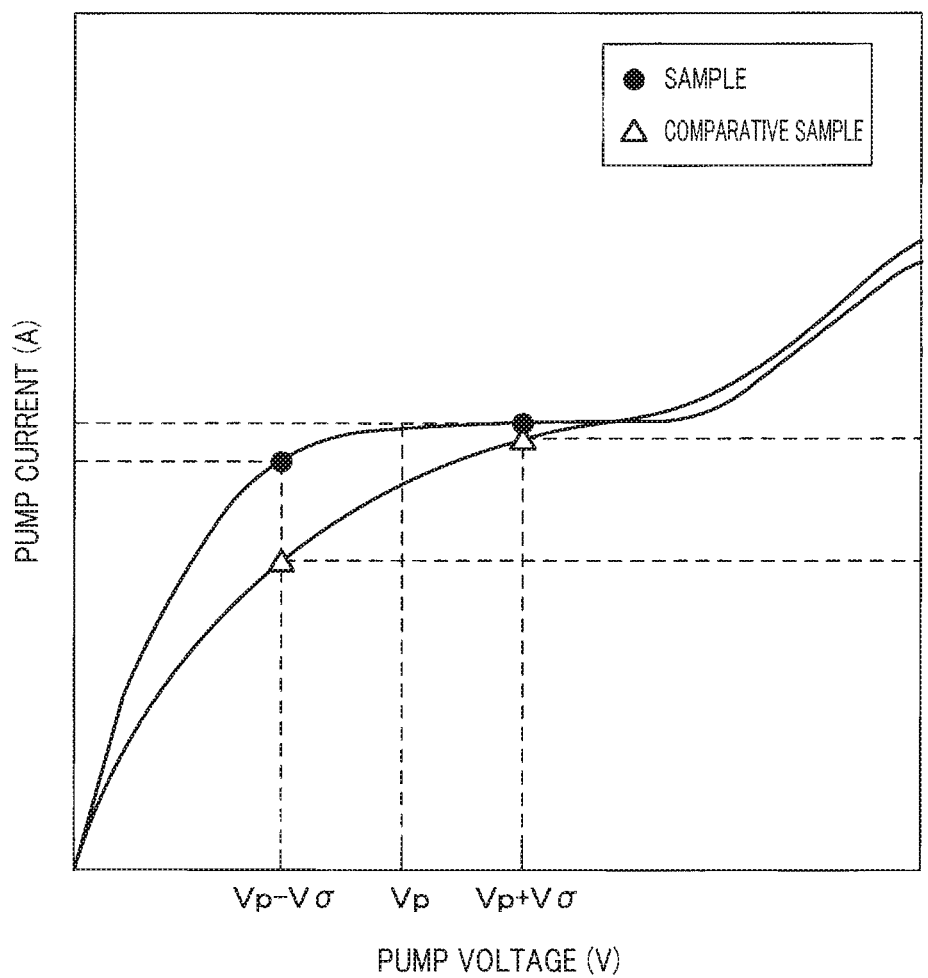
FIG. 11 a pattern graph showing relations between the pump voltage and the pump current after heating at 900° C. for 20 hours according to the experimental example 1.

Next, after heating at 900° C. for 20 hours, a result of investigating a relationship between the pump voltage and a pump current is shown in FIG. 11. As shown in FIG. 11, even if the samples belonging to the present disclosure are heated at 900° C. for 20 hours, the pump current is not greatly changed relative to that before heating (refer to FIG. 9). However, when comparative samples not belonging to the present disclosure are heated for 20 hours, the pump current is largely reduced. That is, oxygen included in the measurement target gases g may be insufficiently discharged. Because the pore of the pump electrode 3 is high in the comparative samples 1 to 5, Au atoms migrate during heating, and the pores of the pump electrode 3 are then filled with Au. Then, a contact area between the pump electrode 3 and the oxygen is reduced.

Figure 12:
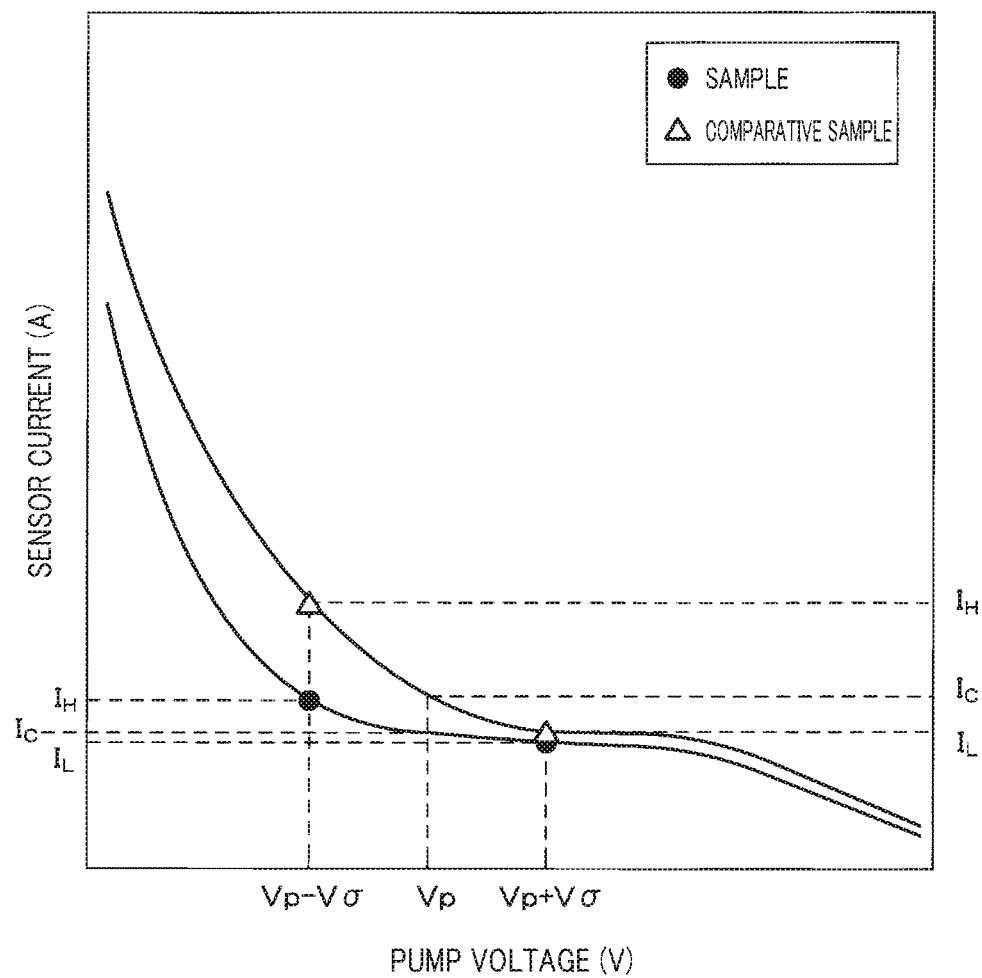
FIG. 12 a pattern graph showing relations between the pump voltage and the sensor current after heating at 900° C. for 20 hours according to the experimental example 1.

Next, after heating at 900° C. for 20 hours, the result of investigating the relationship between the pump voltage and the sensor current is shown in FIG. 12. As shown in FIG. 12, when the sample belonging to the present disclosure is heated at 900° C. for 20 hours, the sensor current thereof is not greatly changed relative to that before heating (refer to FIG. 10). This is because when the sample belonging to the present disclosure is heated, the oxygen discharge capacity is not greatly reduced in the pump cell 30. On the other hand, when the comparative samples not belonging to the present disclosure are heated for 20 hours, the sensor current is increased. This increase occurs because when the comparative samples are heated, the oxygen discharge capacity is reduced in the pump cell 30, and the measurement target gases including much content of oxygen are then moved to the sensor cell 50. Therefore, the sensor current caused by oxygen flows, and the concentration of the specific gases may not be determined accurately.

In this case, a sensor current $I_H$, a sensor current $I_L$ and a sensor current Ic are determined. The sensor current $I_H$ is a sensor current when the pump voltage is Vp−Vσ. The sensor current $I_L$ is a sensor current when the pump voltage is Vp+Vσ. The sensor current $I_c$ is a sensor current when the pump voltage is Vp. A current change ratio ΔI is defined by these measured values as follows.

$$\Delta I = (I_H - I_L)/Ic \times 100$$

In this formula, the concentration of the measurement target gases may be determined accurately as the current change ratio ΔI becomes smaller.

In addition, a current change ratio determined before heating at 900° C. for 20 hours is $\Delta I_B$. A current change ratio determined after heating is $\Delta I_A$. The differences $\Delta I_A - \Delta I_B$ is defined as a durability variation δI.

$$\delta I = \Delta I_A - \Delta I_B$$

In this formula, a measurement accuracy of the specific gases after heating the samples for 20 hours is not reduced as the durability variation δI becomes smaller.

The current change ratios $\Delta I_B$ and $\Delta I_A$ and the durability variation δI were determined for the samples 1 to 4 and the comparative samples 1 to 5. In this case, it is set that Vp=0.38 (V) and Vσ=0.002 (V). In addition, gases including $N_2$ 78%, $O_2$ 20% and NOx 2% were used as the measurement target gases. Measurement results are shown in Table 1. In addition, a relationship between the pore of the pump electrode 3 and the durability variation δI is shown in FIG. 13.

Figure 13:
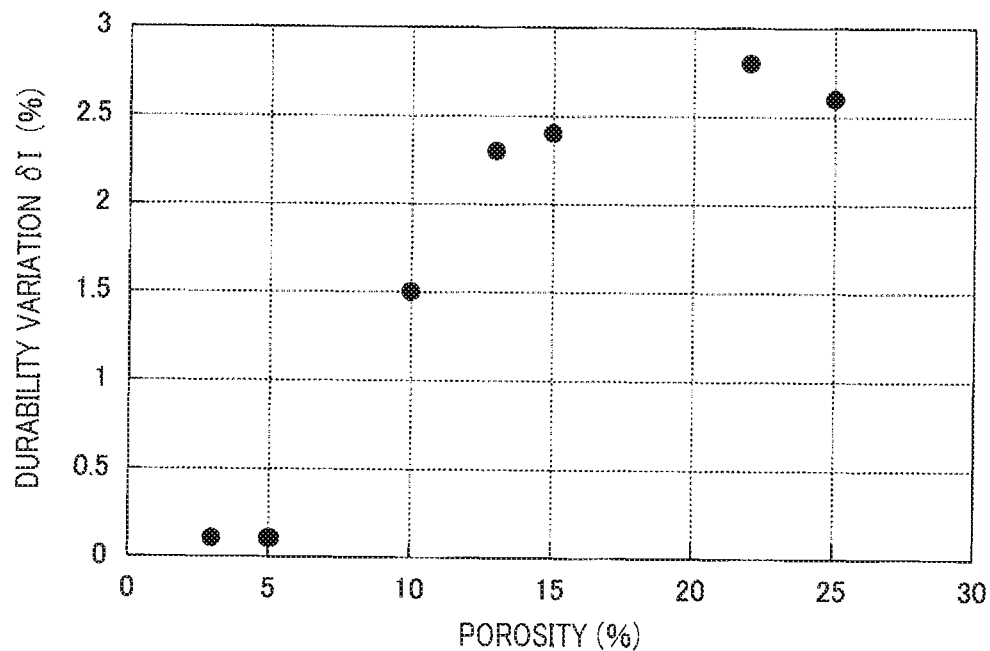
FIG. 13 a pattern graph showing relations between a pore of the pump electrode and durability variation according to the experimental example 1.

As shown in Table 1 and FIG. 13, when the pore of the pump electrode 3 is 5.1% or less, it is shown that the durability variation δI is approximately 0.1%. That is, it is shown that the measurement accuracy of the concentration of the specific gases is not reduced after heating for 20 hours. On the other hand, when the pore of the pump electrode 3 is over 5.1%, it is shown that the durability variation δI is 1.5% or more. That is, it is shown that the measurement accuracy of the concentration of the specific gases after heating for 20 hours is reduced.

Next, a plurality of gas sensors 1 having a structure described in the first embodiment are manufactured. In each of the plurality of gas sensors 1, the surface roughness Ra of the pump electrode 3, the content ratio of an aggregate and the pore are respectively adjusted to values shown in Table 2. Thereby, samples 5 to 10 belonging to the present disclosure and comparative samples 6 to 9 not belonging to the present disclosure are manufactured. The comparative samples 6 to 9 have a surface roughness Ra which is not set in the range of 0.5 μm to 9.1 μm, and therefore they do not belong to the present disclosure.

TABLE 2

| | Surface roughness μm | Aggregate vol % | Porosity vol % | Current change rate ΔI | | Durability variation δI % | Resistance mΩ |
| --- | --- | --- | --- | --- | --- | --- | --- |
| | | | | $\Delta I_A$ % | $\Delta I_B$ % | | |
| Sample 5 | 0.5 | 4.9 | 5.2 | 1.7 | 1.9 | 0.2 | 20 |
| Sample 6 | 0.5 | 30 | 5 | 1.7 | 1.8 | 0.1 | No data |
| Sample 7 | 0.5 | 75 | 5 | 1.8 | 2 | 0.2 | 30 |
| Sample 8 | 5 | 30 | 5 | 1.5 | 1.6 | 0.1 | 23 |
| Sample 9 | 9.1 | 5 | 5.1 | 1.5 | 1.7 | 0.2 | 22 |
| Sample 10 | 9 | 75 | 5.2 | 1.6 | 1.8 | 0.2 | 30 |
| Comparative sample 6 | 0.3 | 5 | 5 | 1.8 | 3.8 | 2 | 22 |
| Comparative sample 7 | 0.3 | 75 | 4.5 | 1.9 | 3.9 | 2 | 30 |
| Comparative sample 8 | 12 | 5 | 4.7 | 1.5 | 4.5 | 3 | 21 |
| Comparative sample 9 | 12 | 75 | 4.9 | 1.5 | 4 | 2.5 | 31 |

In the samples 5 to 10 and the comparative samples 6 to 9, the current change ratio $\Delta I_B$ and $\Delta I_A$ and the durability variation δI are determined similar to Table 1. The results are shown in Table 2. In addition, a relationship between the roughness Ra and the durability variation δI is shown in FIG. 14.

Figure 14:
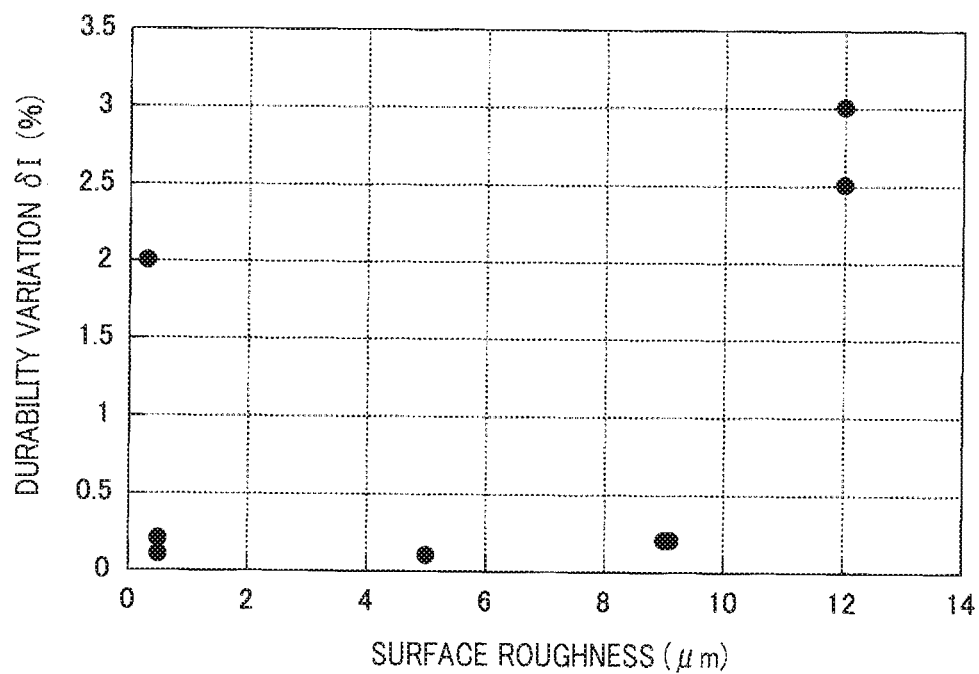
FIG. 14 a pattern graph showing relations between a surface roughness Ra of the pump electrode and the durability variation according to the experimental example 1.

As shown in FIG. 14 and Table 2, when the surface roughness of the pump electrode 3 is set in the range of 0.5 μm to 9.1 μm, it is shown that the durability variation δI is approximately 0.2%. That is, it is shown that the measurement accuracy of the concentration of the specific gases is not reduced after heating for 20 hours. On the other hand, when the surface roughness of the pump electrode 3 is not set in the range of 0.5 μm to 9.1 μm, it is shown that the durability variation δI is 2% or more. That is, it is shown that the measurement accuracy of the concentration of the specific gases is reduced after heating for 20 hours.

Next, the plurality of the gas sensors 1 having the structure described in the first embodiment are manufactured. In each of the plurality of the gas sensors 1, the surface roughness Ra of the pump electrode 3, the content ratio of the aggregate and the pore are respectively adjusted to values shown in Table 3. Thereby, samples 11 to 16 belonging to the present disclosure and comparative samples 10 and 11 not belonging to the present disclosure are manufactured. The comparative samples 10 and 11 have the content ratio of the aggregate which is not 4.9 vol % or more, and therefore they do not belong to the present disclosure.

TABLE 3

|  | Surface roughness μm | Aggregate vol % | Porosity vol % | Current change rate ΔI | | Durability variation δI % | Resistance mΩ |
| --- | --- | --- | --- | --- | --- | --- | --- |
|  |  |  |  | $\Delta I_A$ % | $\Delta I_B$ % |  |  |
| Sample 11 | 0.5 | 4.9 | 5.2 | 1.7 | 1.9 | 0.2 | 20 |
| Sample 12 | 0.5 | 30 | 5 | 1.7 | 1.8 | 0.1 | No data |
| Sample 13 | 0.5 | 75 | 5 | 1.8 | 2 | 0.2 | 30 |
| Sample 14 | 9.1 | 5 | 5.1 | 1.5 | 1.7 | 0.2 | 22 |
| Sample 15 | 9 | 30 | 5.1 | 1.5 | 1.6 | 0.1 | No data |
| Sample 16 | 9 | 75 | 5.2 | 1.6 | 1.8 | 0.2 | 30 |
| Comparative sample 10 | 0.5 | 1 | 4.9 | 3.5 | 5.5 | 2 | 19 |
| Comparative sample 11 | 9 | 1.1 | 4.8 | 3.5 | 5.5 | 2 | 19 |

In the samples 11 to 16 and the comparative samples 10 and 11, the current change ratios $\Delta I_B$ and $\Delta I_A$ and the durability variation δI are determined in the same manner as for Table 1. The result is shown in Table 3. In addition, the relationship between the roughness Ra and the durability variation δI is shown in FIG. 15.

Figure 15:
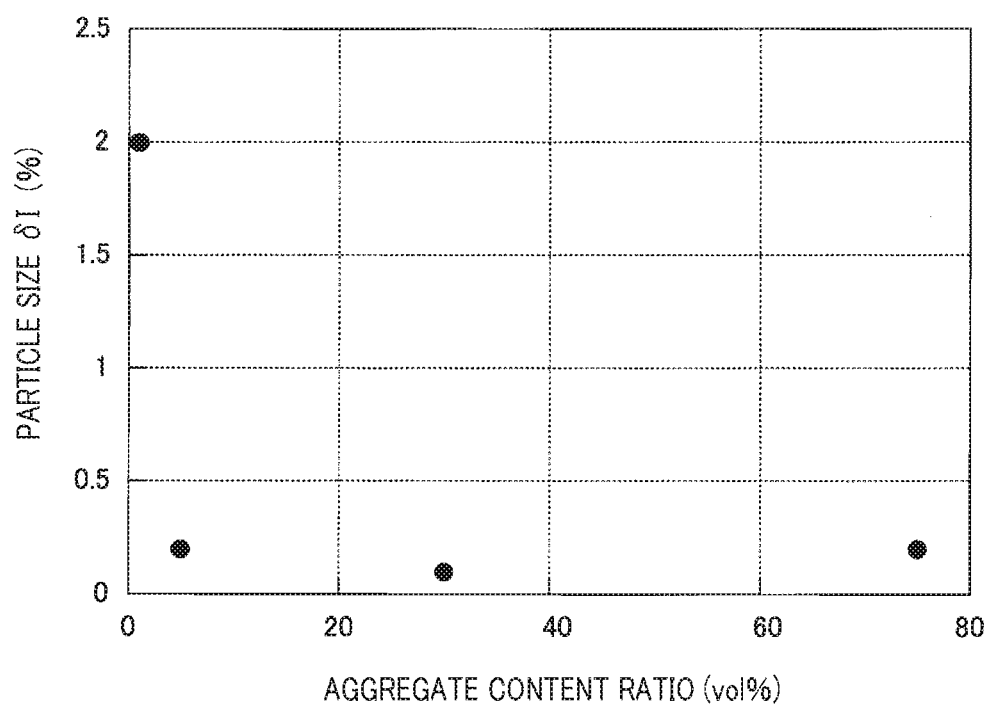
FIG. 15 a pattern graph showing relations between a content ratio of an aggregate of the pump electrode and the durability variation according to the experimental example 1.

As shown in FIG. 15 and Table 3, when the content ratio of the aggregate is 4.9 vol % or more, it is shown that the durability variation δI is approximately 0.2%. That is, it is shown that the measurement accuracy of the concentration of the specific gases is not reduced after heating for 20 hours. On the other hand, when the content ratio of the aggregate is less than 4.9 vol %, it is shown that the durability variation δI is 2%. That is, it is shown that the measurement accuracy of the concentration of the specific gases is reduced after heating for 20 hours.

By the above-described experiment data, before heating the single solid electrolyte 2 at 900° C. for 20 hours, in the pump electrode 3, the pore is set to be 5.2 vol % or less, the surface roughness Ra is set in the range of 0.5 μm to 9.1 μm, and the content ratio of the aggregate 31 is set to be 4.9 vol % or more. In this case, it is shown that the durability variation δI is within 0.2%. That is, it is shown that the measurement accuracy of the concentration of the specific gases is not reduced after heating for 20 hours.

Experiment 2

Two gas sensors 1 having the structure shown in FIG. 1 were manufactured. In each of two gas sensors 1, a surface roughness Ra of a pump electrode 3, a content ratio of an aggregate and a pore were respectively adjusted to values shown in the following Table 4. Thereby, samples 17 and 18 belonging to the present disclosure were manufactured. In addition, electrical resistances of two pump electrodes 3 corresponding to the two gas sensors 1 were determined. The result is shown in Table 4. In addition, in the above-described samples 1 to 16 and the above-described comparative samples 1 to 11, each of electric resistances of pump electrodes 3 were determined. A measurement result is shown in Tables 1 to 3.

Incidentally, a dimension of the pump electrode 3 when the electric resistance of the pump electrode 3 was determined was 2.0 mm×1.0 mm. In addition, powder of zirconia was used as the aggregate included in the pump electrode 3. A particle diameter of the aggregate was set to be 0.5 μm to 5.0 μm.

TABLE 4

|  | Surface roughness μm | Aggregate vol % | Porosity vol % | Resistance mΩ |
| --- | --- | --- | --- | --- |
| Sample 17 | 0.5 | 83 | 4.5 | >1 kΩ |
| Sample 18 | 9.1 | 82 | 4.7 | >1 kΩ |

As shown in Tables 1 to 4, when a content ratio of the aggregate of the pump electrode 3 is 75 vol % or less, it is shown that excessive increase of the electrical resistance of the pump electrode 3 may be avoided. Therefore, it is shown that a content amount of the aggregate is preferably 75 vol % or less.

REFERENCE SIGNS LIST

1: gas sensor
11: measurement target gas chamber
12: reference gas chamber
2: solid electrolyte
3: pump electrode
30: pump cell
31: aggregate
5: sensor electrode
50: sensor cell
6: reference electrode

The invention claimed is:

1. A gas sensor for determining a concentration of specific gases included in measurement target gases comprising:
a measurement target gas chamber into which the measurement target gases are supplied
a reference gas chamber into which reference gases are supplied;
a solid electrolyte that has oxygen ion conductivity, and the solid electrolyte is disposed between the measurement target gas chamber and the reference gas chamber;
a pump electrode and a sensor electrode that are formed on a surface at a side of the measurement target gas chamber on the solid electrolyte; and
a reference electrode that is formed on a surface at a side of the reference gas chamber on the solid electrolyte,
wherein the solid electrolyte, the pump electrode and the reference electrode constitute a pump cell for reducing an oxygen concentration of the measurement target gases,
wherein the solid electrolyte, the sensor electrode and the reference electrode constitute a sensor cell for determining the concentration of the specific gases included in the measurement target gases of which the oxygen concentration is reduced by the pump cell, wherein the pump electrode includes Pt, Au and an aggregate, wherein in the pump electrode, a pore is set to be 5.2 vol % or less, a surface roughness Ra is set in the range of 0.5 μm to 9.1 μm, and a content ratio of the aggregate is set to be 4.9 vol % or more in a state that the pump electrode has not been heated to an activation temperature of the solid electrolyte yet after the gas sensor has been manufactured.

2. The gas sensor as set forth in claim 1, wherein the content ratio of the aggregate of the pump electrode is 4.9 vol % or more and 75.0 vol % or less.

3. A method of manufacturing the gas sensor as set forth in claim 1 comprising:
- a printing step for printing a pump electrode green body, which is the unbaked pump electrode, disposed on a surface of a solid electrolyte green body, which is the unbaked solid electrolyte;
- a processing a surface step for roughing a surface of the pump electrode green body by pressing an irregularity-forming tool of which a surface has fine irregularities to the pump electrode green body;
- an assembling step for assembling a sensor green body, which is the unbaked gas sensor, with the pump electrode green body; and
- a calcination step for forming the gas sensor by calcinating the sensor green body.

4. A method of manufacturing the gas sensor as set forth in claim 3, wherein the calcination step is performed in a low-oxygen atmospheric air at an oxygen concentration of 2 volume % or less; and
- a calcination temperature is set in a range of 1400° C. to 1500° C.

5. The gas sensor as set forth in claim 1, wherein a content ratio of Pt is set in a range of 48.5 wt % to 98.5 wt %.

6. The gas sensor as set forth in claim 1, wherein a content ratio of Au is set in a range of 0.2 wt % to 9.9 wt %.

7. The gas sensor as set forth in claim 1, wherein a particle diameter of the aggregate is set in a range of 0.5 μm to 5.0 μm.

* * * * *